United States Patent
Zhou et al.

(10) Patent No.: US 12,350,407 B2
(45) Date of Patent: Jul. 8, 2025

(54) METHOD FOR MODIFYING HYDROGEL LUBRICATING COATING ON SURFACE OF GENERAL EQUIPMENT, AND HYDROGEL LUBRICATING COATING-MODIFIED GENERAL EQUIPMENT

(71) Applicants: Lanzhou Institute of Chemical Physics, Chinese Academy of Sciences, Lanzhou (CN); Yantai Zhongke Research Institute of Advanced Materials and Green Chemical Engineering, Yantai (CN)

(72) Inventors: Feng Zhou, Lanzhou (CN); Shuanhong Ma, Lanzhou (CN); Yunlei Zhang, Lanzhou (CN); Zhengfeng Ma, Lanzhou (CN)

(73) Assignees: Lanzhou Institute of Chemical Physics, Chinese Academy of Sciences (CN); Yantai Zhongke Research Institute of Advanced Materials and Green Chemical Engineering (CN)

(*) Notice: Subject to any disclaimer, the term of this patent is extended or adjusted under 35 U.S.C. 154(b) by 473 days.

(21) Appl. No.: 18/061,059

(22) Filed: Dec. 2, 2022

(65) Prior Publication Data
US 2023/0173138 A1  Jun. 8, 2023

(30) Foreign Application Priority Data
Dec. 6, 2021 (CN) .......................... 202111511558.2

(51) Int. Cl.
*A61L 31/14* (2006.01)
*A61L 27/34* (2006.01)
(Continued)

(52) U.S. Cl.
CPC ............. *A61L 31/145* (2013.01); *A61L 27/34* (2013.01); *A61L 27/52* (2013.01); *A61L 29/085* (2013.01);
(Continued)

(58) Field of Classification Search
CPC ........ A61L 31/145; A61L 27/34; A61L 27/52; A61L 29/085; A61L 29/145; A61L 31/10;
(Continued)

(56) References Cited

U.S. PATENT DOCUMENTS

| 4,373,009 A | 2/1983 | Winn |
| 2002/0120333 A1* | 8/2002 | Keogh ................... A61L 27/34 |
| | | 604/266 |

(Continued)

FOREIGN PATENT DOCUMENTS

| CN | 104448375 | 3/2015 |
| CN | 104857571 | 8/2015 |

OTHER PUBLICATIONS

Yu, Yan, et al., "Multifunctional 'Hydrogel Skins' on Diverse Polymers with Arbitrary Shapes", Advanced Materials, vol. 31, No. 7, Feb. 15, 2019.

*Primary Examiner* — John D Freeman
(74) *Attorney, Agent, or Firm* — Emerson, Thompson & Bennett, LLC; Roger D. Emerson; Peter R. Detorre (57) ABSTRACT

The present disclosure provides a method for modifying a hydrogel lubricating coating on a surface of general equipment, and hydrogel lubricating coating-modified general equipment, belonging to the technical field of material surface modification. In the present disclosure, by combining catechol adhesion chemistry and free radical polymerization initiated by surface catalysis, the method can realize in-situ generation of free radicals at an interface of a substrate and a hydrogel monomer solution at room tem-
(Continued)

perature, without external auxiliary conditions such as illumination or heating. The method can prepare the hydrophilic hydrogel lubricating coating on the surface of almost all existing substrates, which is especially suitable for lubricating modification on an inner surface of a non-translucent pipeline instrument, showing material versatility. Therefore, the method is suitable for the fields of surface engineering and biomedicine.

20 Claims, 3 Drawing Sheets (51) Int. Cl.
*A61L 27/52* (2006.01)
*A61L 29/08* (2006.01)
*A61L 29/14* (2006.01)
*A61L 31/10* (2006.01)

(52) U.S. Cl.
CPC ............. *A61L 29/145* (2013.01); *A61L 31/10* (2013.01); *A61L 2400/10* (2013.01); *A61L 2420/02* (2013.01); *A61L 2420/08* (2013.01)

(58) Field of Classification Search
CPC ............. A61L 2400/10; A61L 2420/02; A61L 2420/08; A61L 2400/18; C08F 220/281; C08F 220/56
See application file for complete search history.

(56) References Cited

U.S. PATENT DOCUMENTS

2007/0225823 A1\* 9/2007 Hawkins ................. A61L 27/28
428/420
2014/0221522 A1\* 8/2014 Antoni .................... A61L 31/10
523/105

\* cited by examiner

METHOD FOR MODIFYING HYDROGEL LUBRICATING COATING ON SURFACE OF GENERAL EQUIPMENT, AND HYDROGEL LUBRICATING COATING-MODIFIED GENERAL EQUIPMENT

CROSS REFERENCE TO RELATED APPLICATION

This patent application claims the benefit and priority of Chinese Patent Application No. 202111511558.2, filed with the China National Intellectual Property Administration on Dec. 6, 2021, the disclosure of which is incorporated by reference herein in its entirety as part of the present application.

TECHNICAL FIELD

The present disclosure relates to the technical field of material surface modification, in particular to a method for modifying a hydrogel lubricating coating on a surface of general equipment, and hydrogel lubricating coating-modified general equipment.

BACKGROUND

The aging population puts forward an urgent demand for implanted and interventional medical devices and materials. Medical devices are generally in direct contact with the surface of human tissues during implantation and intervention. The biocompatibility, mechanical modulus, and lubricating properties of the device surface may greatly affect the comfort of patients during use. In order to ensure the strength of mechanical support, the primary molding equipment generally has a large surface modulus, and does not match soft tissues of the human body. During the implantation and intervention, tissue damages, constriction, and foreign body sensation are likely to occur due to stress difference. In addition, the primary molding device usually has an inert surface being bare metals and polymers, which lacks desirable lubricating properties. The implantation and intervention generally produces high frictional resistance with the surface of organ tissues, bringing great pains to the patient. Accordingly, it is of great significance to modify the surface of medical equipment.

At present, the most effective way to improve the lubricity and comfort of implanted and interventional medical devices is to modify the surface of devices with a biocompatible, mechanical modulus-compatible, and soft-substance hydrophilic polymer coating. Hydrogel is a hydrophilic polymer-based cross-linked network containing a large number of water molecules, with a water content reaching not less than 70%. The high water content of the hydrogel can make its surface have desirable water lubricity, thereby greatly reducing the friction between a solid and a contact surface; the polymer network of the hydrogel leads to softness and elasticity, which is similar to the natural tissues and organs, such as muscle, cartilage, and skin in biological tissues, such that the hydrogel has excellent mechanical matching with the biological tissues. Meanwhile, the desirable biocompatibility endows hydrogels with application prospects as a medical material. Due to these characteristics, hydrogel coatings have a desirable potential for use in the fields of biomedical equipment and organizational engineering.

Currently, the common technical means for the surface lubrication modification of medical equipment is to apply a hydrophilic polymer coating on a surface of the equipment, such as the methods in Patent CN104857571A, CN104448375A, and U.S. Pat. No. 4,373,009. However, these methods, basically based on polyvinylpyrrolidone (PVP), silicone, and PVC and other materials, do not have the universality of base materials and have a complicated preparation process. An existing technology (Yan Yu, Hyun-woo Yuk, German A. Parada, You Wu, Xinyue Liu, Christoph S. Nabzdyk, Kamal Youcef-Toumi, Jianfeng Zang, Xuanhe Zhao, Multifunctional "hydrogel skins" on diverse polymers with arbitrary shapes, *Advanced Materials*, 31 (7): 1807101, 2019) reports a method for modifying a hydrogel coating on a surface of a polymer duct through photo-initiation. However, this modification technology is only suitable for polymer substrates that can be swollen by organic solvents, such as polyvinyl chloride (PVC), polyurethane (PU), or silicone, showing no universality of substrate modification. More importantly, photopolymerization technology has not been able to achieve water-lubrication modification of the inner surface of non-translucent pipeline instruments so far, becoming a technical bottleneck in the field.

SUMMARY

An objective of the present disclosure is to provide a method for modifying a hydrogel lubricating coating on a surface of general equipment, and hydrogel lubricating coating-modified general equipment. On the premise of not changing the body and surface properties of a substrate, the method can prepare a hydrophilic hydrogel lubricating layer on the surface of various substrates, showing material versatility.

To achieve the above objective of the present disclosure, the present disclosure provides the following technical solutions.

The present disclosure provides a method for modifying a hydrogel lubricating coating on a surface of general equipment, including the following steps:

depositing an adhesive solution of a catechol group-containing polymer on a surface of a substrate, to obtain a polyphenol coating-deposited substrate; wherein the substrate is general equipment; and compounding the polyphenol coating-deposited substrate with a hydrogel monomer solution, and conducting in-situ polymerization to obtain a hydrogel lubricating coating-modified substrate; wherein the hydrogel monomer solution comprises persulfates and transition metal ions.

Preferably, a material of the general equipment includes a natural material and an artificial material; and the artificial material is selected from the group consisting of an inorganic metal material, an inorganic non-metallic material, and an organic polymer.

Preferably, in the adhesive solution, the catechol group-containing polymer is a poly(dopamine methacrylamide-methoxyethyl acrylate) copolymer; and a preparation method of the poly(dopamine methacrylamide-methoxyethyl acrylate) copolymer includes the following steps:

mixing dopamine methacrylamide, methoxyethyl acrylate, and azobisisobutyronitrile with an organic solvent, and conducting free radical polymerization to obtain the poly(dopamine methacrylamide-methoxyethyl acrylate) copolymer; wherein the dopamine methacrylamide and the methoxyethyl acrylate have a mass ratio of (0.5-2.0):(1.0-15); and the free radical polymerization is conducted at 50° C. to 80° C. for 6 h to 18 h.

Preferably, the adhesive solution of the catechol group-containing polymer has a solvent being one or more selected from the group consisting of methanol, ethanol, isopropanol, dichloromethane, dichloroethane, trichloroethane, N,N-dimethylformamide, dimethyl sulfoxide, N-methylpyrrolidone, tetrahydrofuran, ethyl acetate, and butyl acetate, and has a mass concentration of 1% to 50%.

Preferably, the hydrogel monomer solution includes the following components by mass percentage: 5% to 60% of a monomer, 0.01% to 5% of a transition metal ion, 0.02% to 5% of an initiator, 0.01% to 1% of a cross-linking agent, and water as a balance.

Preferably, the monomer is one or more selected from the group consisting of acrylic acid, methacrylic acid, acrylamide, hydroxyethyl acrylate, hydroxyethyl methacrylate, polyoxyethylene methacrylate, N-isopropylacrylamide, 2-acrylamido-2-methylpropanesulfonic acid, 2-acrylamido-2-methylpropanesulfonate, methacrylate sulfonate, chitosan acrylate, chitosan methacrylate, dimethylaminoethyl methacrylate, sodium methacrylate alginate, methacryloylethyl carboxybetaine, and methacryloylethyl sulfobetaine.

Preferably, the initiator is potassium persulfate and/or ammonium persulfate; and the cross-linking agent is N,N'-methylenebisacrylamide and/or polyethylene glycol dimethacrylate.

Preferably, the transition metal ion is one or more selected from the group consisting of $Fe^{3+}$, $Ag^+$, $Cu^{2+}$, $Cu^+$, $Ru^{3+}$, $Mn^{2+}$, $Co^{2+}$, and $Ni^{2+}$.

Preferably, the in-situ polymerization is conducted at −10° C. to 40° C. for 0.5 min to 30 min.

The present disclosure further provides hydrogel lubricating coating-modified general equipment prepared by the method, including general equipment and a hydrogel lubricating coating modified on a surface of the general equipment; where the hydrogel lubricating coating includes a polymeric micelle-based polyphenol coating and a hydrogel coating that are sequentially laminated on the surface of the general equipment.

The present disclosure provides a method for modifying a hydrogel lubricating coating on a surface of general equipment, including the following steps: depositing an adhesive solution of a catechol group-containing polymer on a surface of a substrate, to obtain a polyphenol coating-deposited substrate; where the substrate is general equipment; and compounding the polyphenol coating-deposited substrate with a hydrogel monomer solution, and conducting in-situ polymerization to obtain a hydrogel lubricating coating-modified substrate; where the hydrogel monomer solution includes persulfates and transition metal ions. In the present invention, the adhesive solution of the catechol group-containing polymer is easy to adhere to the surfaces of various substrates, the catechol group-containing polyphenol coating has a coordination mechanism with transition metal ions in the hydrogel monomer solution, and the catechol groups on a surface of the polyphenol coating undergo a Fenton reaction with the transition metal ions and persulfates to generate free radicals in situ. Therefore, under the combined action of these two mechanisms, high-concentration interfacial free radicals are generated on the polyphenol coating, resulting in polymerization of the monomers in the hydrogel monomer solution on the surface of the polyphenol coating; the hydrogel coating is grown in situ on the surface of the polyphenol coating of the substrate, while the monomer solution far from the surface of the substrate does not polymerize, so as to avoid the influence on the properties of the substrate. Accordingly, the method can realize in-situ generation of free radicals at an interface of a substrate and a hydrogel monomer solution at room temperature, without external auxiliary conditions such as illumination or heating. The method can prepare the hydrogel lubricating coating on the surface of various materials and devices, which is especially suitable for lubricating modification on an inner surface of a non-translucent pipeline instrument, showing material versatility.

In the existing photo-initiating methods, conditions such as ultraviolet rays may generate a lot of heat during use, causing thermal polymerization of the bulk solution, and making the reaction uncontrollable; while the method of the present disclosure has a simple preparation process and mild reaction conditions, and requires no UV initiation and heating and does not initiate bulk solution polymerization; and the formed hydrogel lubricating coating has a controllable thickness.

In the existing method, metal catalysts including the iron powder, as active sites, are added to the substrate to grow a hydrogel lubricating layer in situ, but the metal doping may change inherent characteristics of the substrate; while the method of the present disclosure does not require pre-doping catalysts in the substrate, which does not change bulk and surface properties of the substrate.

DETAILED DESCRIPTION OF THE EMBODIMENTS

The present disclosure provides a method for modifying a hydrogel lubricating coating on a surface of general equipment, including the following steps:
depositing an adhesive solution of a catechol group-containing polymer on a surface of a substrate, to obtain a polyphenol coating-deposited substrate; wherein the substrate is general equipment; and
compounding the polyphenol coating-deposited substrate with a hydrogel monomer solution, and conducting in-situ polymerization to obtain a hydrogel lubricating coating-modified substrate; wherein the hydrogel monomer solution comprises persulfates and transition metal ions.

In the present disclosure, unless otherwise specified, all raw materials required for preparation are commercially available products well known to persons skilled in the art.

In the present disclosure, an adhesive solution of a catechol group-containing polymer is deposited on a surface of a substrate, to obtain a polyphenol coating-deposited substrate. The substrate is general equipment; a material of the general equipment includes preferably a natural material and an artificial material; there is no special limitation on a type of the natural material, and any natural material in the field of biomedical equipment and tissue engineering well-known in the art can be used.

In the present disclosure, the artificial material is preferably selected from the group consisting of an inorganic metal material, an inorganic non-metallic material, and an organic polymer; the inorganic metal material is preferably selected from the group consisting of aluminum, titanium, copper, and iron; the inorganic non-metallic material is preferably selected from the group consisting of glass and silicon wafer; and the organic polymer is preferably selected from the group consisting of polyethylene terephthalate, an ethylene-ethyl acetate copolymer, polyimide, nylon, polydimethylsiloxane, polyethylene, polymethylmethacrylate, polypropylene, and polytetrafluoroethylene.

In the present disclosure, there is no special limitation on a type of the general equipment, and both biomedical equipment and equipment in the field of tissue engineering can be used; the universal equipment includes preferably a urinary catheter, a drainage catheter, or an implanted and interventional cannula.

In the present disclosure, in the adhesive solution, the catechol group-containing polymer is preferably a poly(dopamine methacrylamide-methoxyethyl acrylate) copolymer; and a preparation method of the poly(dopamine methacrylamide-methoxyethyl acrylate) copolymer includes preferably the following steps:

mixing dopamine methacrylamide, methoxyethyl acrylate, and azobisisobutyronitrile with an organic solvent, and conducting free radical polymerization to obtain the poly(dopamine methacrylamide-methoxyethyl acrylate) copolymer.

In the present disclosure, the dopamine methacrylamide and the methoxyethyl acrylate have a mass ratio of preferably (0.5-2.0):(1.0-15), more preferably (0.5-1.7):(1.0-7.5); and the azobisisobutyronitrile has a mass of preferably 0.2% to 5%, more preferably 2.2% to 3% of a total mass of the dopamine methacrylamide and the methoxyethyl acrylate.

In the present disclosure, the organic solvent is preferably N,N-dimethylformamide; there is no special limitation on an amount of the organic solvent, as long as the reaction can be ensured smoothly.

In the present disclosure, there is no special limitation on a mixing process of the dopamine methacrylamide, the methoxyethyl acrylate, the azobisisobutyronitrile, and the organic solvent, and the materials can be uniformly mixed according to a process well known in the art.

In the present disclosure, the free radical polymerization is conducted at preferably 50° C. to 80° C., more preferably 60° C. to 75° C. for preferably 6 h to 18 h, more preferably 12 h.

In the present disclosure, after the free radical polymerization is completed, an obtained product is preferably poured into a methanol-diethyl ether mixed solvent, precipitated, and vacuum-dried to obtain the poly(dopamine methacrylamide-methoxyethyl acrylate) copolymer. In the methanol-diethyl ether mixed solvent, methanol and diethyl ether have a volume ratio of preferably 1:(10-40); and the vacuum drying is conducted at preferably 40° C. There is no special limitation on a precipitation time, as long as the materials can be fully precipitated.

In the present disclosure, the adhesive solution of the catechol group-containing polymer has a solvent preferably being one or more selected from the group consisting of methanol, ethanol, isopropanol, dichloromethane, dichloroethane, trichloroethane, N,N-dimethylformamide, dimethyl sulfoxide, N-methylpyrrolidone, tetrahydrofuran, ethyl acetate, and butyl acetate; when the solvent is a mixture of two or more of the above, there is no special limitation on a ratio of different types of solvents, and any ratio can be used.

In the present disclosure, the adhesive solution of the catechol group-containing polymer has a mass concentration of preferably 1% to 50%, more preferably 5% to 10%. There is no special limitation on an amount of the adhesive solution of the catechol group-containing polymer, as long as the adhesive solution can be sufficiently deposited on the surface of the substrate.

In the present disclosure, there is no special limitation on a deposition method, and the method can be adjusted according to a specific structure of the general equipment according to the process well known in the art, such that uniform deposition can be achieved; in an example, the deposition is conducted by coating. There is no special limitation on a thickness of a polyphenol coating formed by the deposition, and the thickness can be adjusted according to actual needs.

During the deposition, a catechol group-containing polymeric micelle adheres to the surface of the substrate to form a polyphenol coating; and the polyphenol coating can be used as a hydrogel reaction site while ensuring desirable bonding with the substrate, so as to facilitate the subsequent formation of a hydrogel lubricating coating.

In the present disclosure, after the deposition is completed, an obtained substrate is preferably dried at a room temperature to obtain a polyphenol coating-deposited substrate; there is no special limitation on a drying time, and the time can be adjusted according to actual needs; in an example, the drying is conducted for 12 h.

In the present disclosure, the polyphenol coating-deposited substrate is compounded with a hydrogel monomer solution, and in-situ polymerization is conducted to obtain a hydrogel lubricating coating-modified substrate.

In the present disclosure, the hydrogel monomer solution includes persulfates and transition metal ions; the hydrogel monomer solution includes preferably the following components by mass percentage: 5% to 60% of a monomer, 0.01% to 5% of a transition metal ion, 0.02% to 5% of an initiator, 0.01% to 1% of a cross-linking agent, and water as a balance.

In the present disclosure, in terms of mass percentage, preferably 17.6% to 20% of the monomer, preferably 0.08% to 0.1% of the transition metal ion, preferably 0.16% to 0.9% of the initiator, and preferably 0.08% to 0.125% of the cross-linking agent are used.

In the present disclosure, the monomer is preferably one or more selected from the group consisting of acrylic acid, methacrylic acid, acrylamide, hydroxyethyl acrylate, hydroxyethyl methacrylate, polyoxyethylene methacrylate, N-isopropylacrylamide, 2-acrylamido-2-methylpropanesulfonic acid, 2-acrylamido-2-methylpropanesulfonate, methacrylate sulfonate, chitosan acrylate, chitosan methacrylate, dimethylaminoethyl methacrylate, sodium methacrylate alginate, methacryloylethyl carboxybetaine, and methacryloylethyl sulfobetaine; when the monomer is a mixture of two or more of the above, there is no special limitation on a ratio of different types of monomers, and any ratio can be used. There is no special limitation on a source and a specific molecular weight of the monomer, and the monomer can be prepared or customized according to actual needs by the well-known preparation process.

In the present disclosure, the transition metal ion is preferably one or more selected from the group consisting of $Fe^{3+}$, $Ag^+$, $Cu^{2+}$, $Cu^+$, $Ru^{3+}$, $Mn^{2+}$, $Co^{2+}$, and $Ni^{2+}$; when the transition metal ion is a mixture of two or more of the above, there is no special limitation on a ratio of different types of transition metal ions, and any ratio can be used. There is no special limitation on a type of a transition metal salt corresponding to the transition metal ion in the hydrogel monomer solution, and water-soluble salts corresponding to the transition metal ion well known in the art can be used; in an example, the water-soluble salt is a chloride salt.

In the present disclosure, the initiator is preferably potassium persulfate and/or ammonium persulfate; the cross-linking agent is preferably N,N'-methylenebisacrylamide and/or polyethylene glycol dimethacrylate; when the initiator is a mixture of two of the above, there is no special limitation on a ratio of different types of initiators, and any ratio can be used; when the cross-linking agent is a mixture of two of the above, there is no special limitation on a ratio of different types of cross-linking agents, and any ratio can be used.

In the present disclosure, there is no special limitation on a preparation process of the hydrogel monomer solution, and hydrogel monomer solutions in the above content range can be prepared according to a process well known in the art.

In the present disclosure, there is no special limitation on an amount of the hydrogel monomer solution, as long as the hydrogel monomer solution is in complete contact with the polyphenol coating-deposited substrate. There is no special limitation on a method for compounding the polyphenol coating-deposited substrate with the hydrogel monomer solution, and the polyphenol coating-deposited substrate and the hydrogel monomer solution are in complete contact according to a process well known in the art; preferably, the method for compounding is adjusted according to the structure of different general equipment.

In the present disclosure, the in-situ polymerization is conducted at preferably −10° C. to 40° C., more preferably 5° C. to 20° C. for preferably 0.5 min to 30 min, more preferably 5 min to 20 min.

During the in-situ polymerization, the polyphenol coating is coordinated to the transition metal ion in the hydrogel monomer solution, and the catechol groups on a surface of the polyphenol coating undergo a Fenton reaction with the transition metal ions and persulfates to generate free radicals in situ. Therefore, under the combined action of the coordination and generation of free radicals, high-concentration interfacial free radicals are generated on the polyphenol coating, resulting in polymerization of the monomers in the hydrogel monomer solution on the surface of the polyphenol coating; the hydrogel lubricating coating is grown in situ on the surface of the substrate, while the monomer solution far from the surface of the substrate does not polymerize, so as to avoid the influence on the properties of the substrate.

In the present disclosure, after the in-situ polymerization is completed, preferably without post-treatment, the hydrogel lubricating coating-modified general equipment is obtained.

The present disclosure further provides hydrogel lubricating coating-modified general equipment prepared by the method, including general equipment and a hydrogel lubricating coating modified on a surface of the general equipment; where the hydrogel lubricating coating includes a polymeric micelle-based polyphenol coating and a hydrogel coating that are sequentially laminated on the surface of the general equipment. The hydrogel lubricating coating has a thickness of preferably 100 μm to 500 μm.

The technical solutions of the present disclosure will be described below clearly and completely in conjunction with the examples of the present disclosure. Apparently, the described examples are only a part of, not all of, the examples of the present disclosure. All other embodiments obtained by those of ordinary skill in the art based on the embodiments of the present disclosure without creative efforts shall fall within the protection scope of the present disclosure.

Example 1

Growth of a polyacrylamide-based hydrogel lubricating coating on a glass surface:
1. 7 g of dopamine methacrylamide, 7.5 g of methoxyethyl acrylate, and 0.1 g of azobisisobutyronitrile were dissolved in 20 mL of N,N-dimethylformamide, and subjected to free radical polymerization at 65° C. for 12 h; an obtained reaction product was precipitated using a mixed solvent including 50 mL of methanol and 500 mL of diethyl ether, and vacuum-dried at 40° C. to obtain a poly(dopamine methacrylamide-methoxyethyl acrylate) copolymer;
the poly(dopamine methacrylamide-methoxyethyl acrylate) copolymer was dissolved in dichloromethane to obtain an adhesive solution with a mass concentration of 5%; the adhesive solution was coated on a surface of a glass substrate, dried at a room temperature for 12 h, such that a polyphenol coating was formed on the surface of the glass substrate; and
2. 16 g of acrylamide, 0.06 g of ferric chloride, 0.01 g of N,N'-methylenebisacrylamide, and 20 mg of potassium persulfate were dissolved in 10 mL of deionized water to obtain a hydrogel monomer solution; the polyphenol coating-deposited glass substrate was immersed in the hydrogel monomer solution, and subjected to in-situ polymerization at 20° C. for different times to form the polyacrylamide-based hydrogel lubricating coating.

Example 2

This example differed from Example 1 only in that: the polyphenol coating-deposited glass substrate was immersed in the hydrogel monomer solution, and subjected to in-situ polymerization at 5° C. for different times to form the hydrogel lubricating coating, while other conditions were the same as those in Example 1.

Example 3

This example differed from Example 1 only in that: the in-situ polymerization was conducted for 5 min, and the substrates used were polyethylene terephthalate, an ethylene-ethyl acetate copolymer, polyimide, nylon, polydimethylsiloxane, polyethylene, polymethylmethacrylate, polypropylene, and polytetrafluoroethylene, while other conditions were the same as those in Example 1.

Example 4

Growth of a polyacrylamide-based hydrogel lubricating coating on an inner surface of a latex catheter device:
2.2 g of a dopamine methacrylamide monomer, 6.5 g of methoxyethyl acrylate monomer, and 0.20 g of azobisisobutyronitrile were dissolved in 30 mL of N,N-dimethylformamide, and subjected to free radical polymerization at 60° C. for 12 h; an obtained reaction product was precipitated using a mixed solvent including 50 mL of methanol and 500 mL of diethyl ether, and vacuum-dried at 40° C. to obtain a poly(dopamine methacrylamide-methoxyethyl acrylate) copolymer;

the poly(dopamine methacrylamide-methoxyethyl acrylate) copolymer was dissolved in dichloromethane to obtain an adhesive solution with a mass concentration of 10%; the adhesive solution was modified on an inner surface of a latex urinary catheter using a peristaltic pump by a microfluidic coating method, and dried at room temperature for 12 h to form a polyphenol coating on the inner surface of the latex urinary catheter; and 6.6 g of acrylamide, 0.06 g of ferric chloride, 0.04 g of N,N'-methylenebisacrylamide, and 30 mg of potassium persulfate were dissolved in 25 mL of deionized water to obtain a hydrogel monomer solution; the hydrogel monomer solution was injected into a cavity of the latex urinary catheter whose inner surface was modified with the polyphenol coating using a peristaltic pump by means of microfluidic injection, and subjected to in-situ polymerization at 20° C. for 3 min to form the polyacrylamide-based hydrogel lubricating coating.

Characterization and Performance Test

Figure 1:
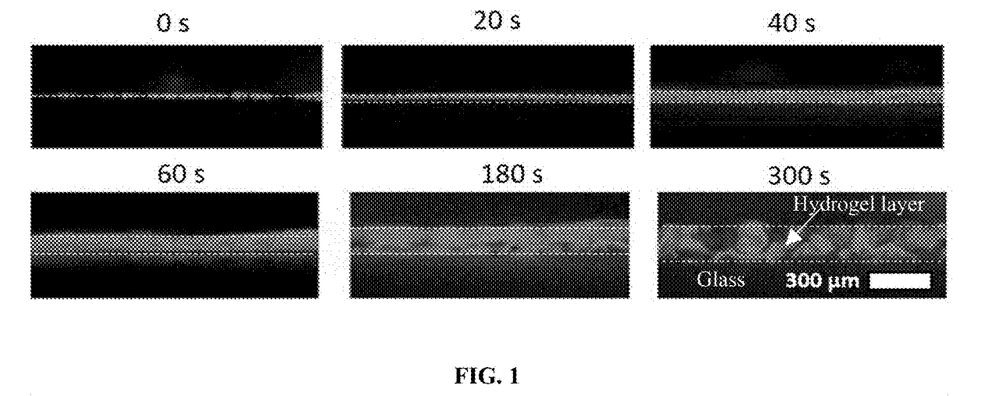
FIG. 1 shows optical microscope photos of polyacrylamide-based hydrogel lubricating coatings grown on a surface of a glass substrate at different reaction times in Example 1.

1) Optical microscopic tests were conducted on the hydrogel lubricating coatings formed in Example 1 at different reaction times, and an uncoated glass substrate was used as a control (a reaction time was 0 sec), and the results were shown in FIG. 1; FIG. 1 showed optical microscope photos of polyacrylamide-based hydrogel lubricating coatings grown on a surface of the glass substrate at different reaction times; it was seen from FIG. 1 that with prolongation of the reaction time, a thickness of the polyacrylamide-based hydrogel lubricating coating gradually increased, and when the reaction time was 300 sec, the thickness of the hydrogel lubricating coating reached 260 μm.

Figure 2:
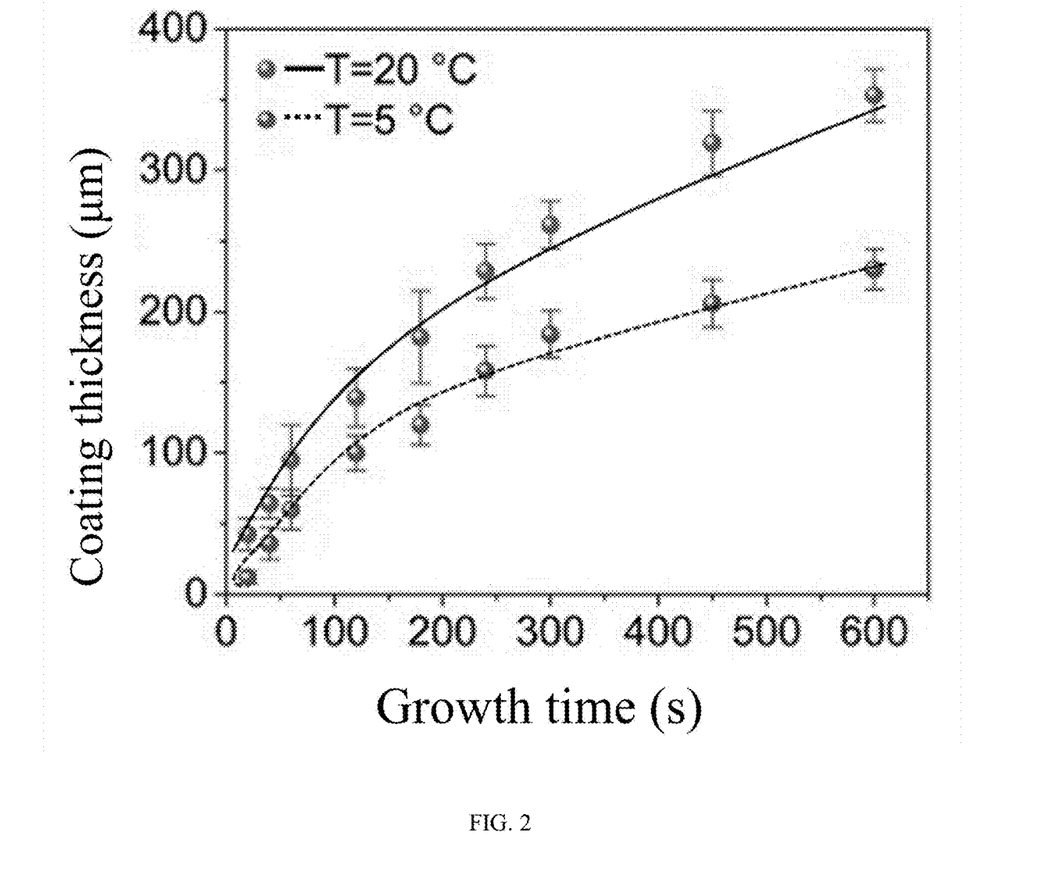
FIG. 2 shows kinetic curves of the polyacrylamide-based hydrogel lubricating coatings grown on a glass surface at different temperatures in Examples 1 and 2.

2) In different in-situ polymerization time ranges, the thickness of the polyacrylamide-based hydrogel lubricating coatings formed in Examples 1 and 2 was tested, and obtained kinetic curves were shown in FIG. 2; FIG. 2 showed kinetic curves of the polyacrylamide-based hydrogel lubricating coatings grown on a glass surface at different temperatures in Examples 1 and 2; as shown in FIG. 2, the thickness of the polyacrylamide gel increased with the reaction time at different temperatures, indicating that the thickness of the hydrogel lubricating coating was highly controllable;

It was seen from FIG. 2 that when the in-situ polymerization reaction temperature was reduced from 20° C. to 5° C., a growth rate of the polyacrylamide-based hydrogel lubricating coating was significantly slowed down; when reacting for 600 sec, the thickness of the polyacrylamide-based hydrogel lubricating coating was 340 μm at 20° C., while the thickness of the polyacrylamide-based hydrogel lubricating coating was only 220 μm at 5° C., indicating that the low temperature might reduce the growth rate of hydrogel lubricating coatings.

Figure 3:
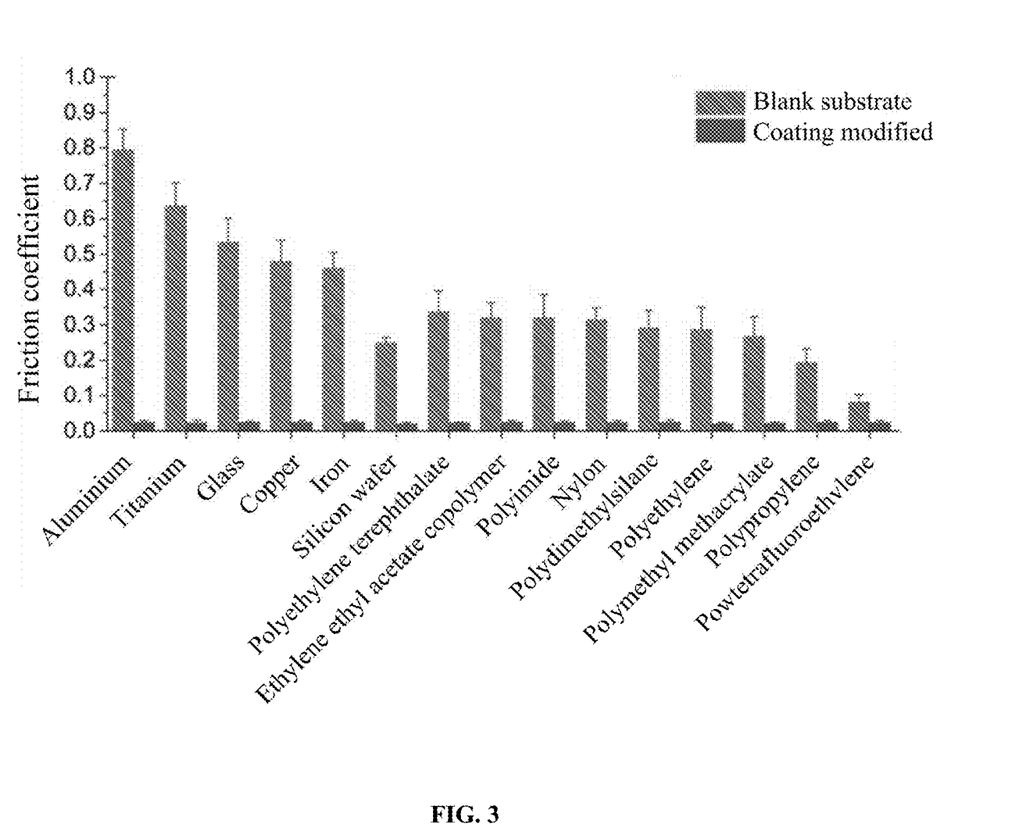
FIG. 3 shows a comparison of friction coefficients before and after of the polyacrylamide-based hydrogel lubricating coatings grown on the surface of various substrates in Example 3.
Figure 4A:
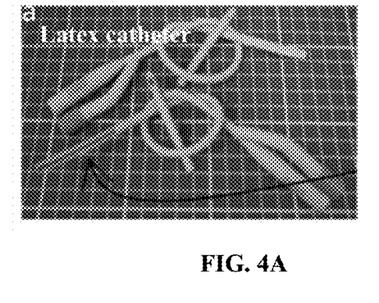
FIG. 4A-D show actual photos of a latex catheter (FIG. 4A) and its inner surface (FIG. 4B), and an optical microscope photo (FIG. 4C) and a scanning electron microscopy (SEM) image (FIG. 4D) of the polyacrylamide-based hydrogel coating on the inner surface of the latex catheter in Example 4.
Figure 4B:
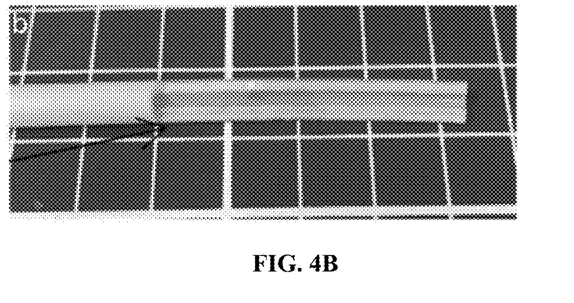
Figure 4C:
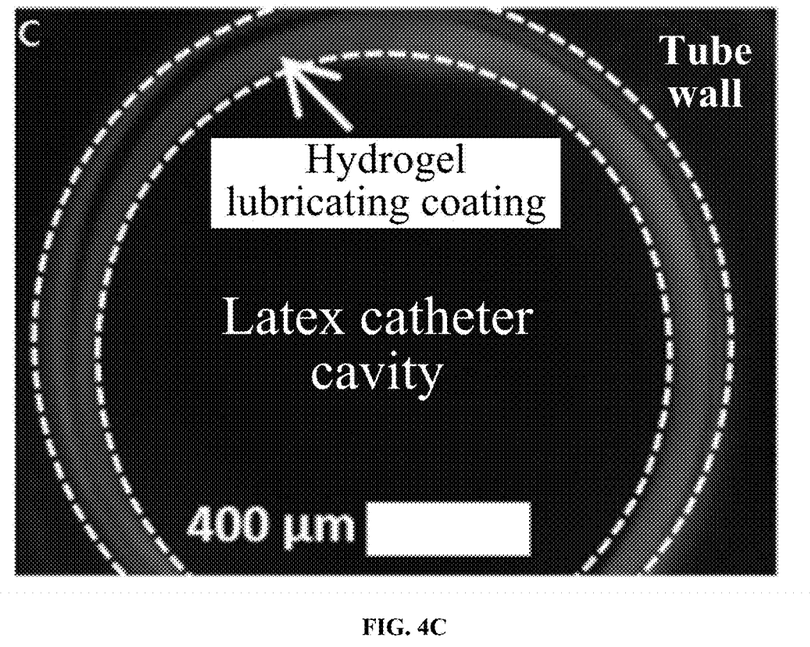
Figure 4D:
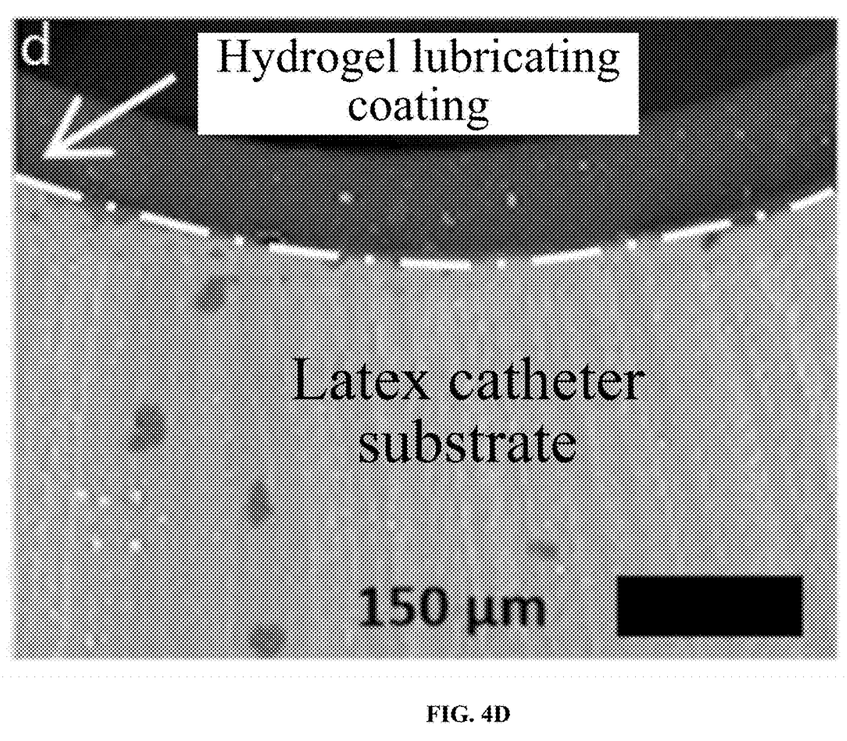

3) The lubricating properties of the polyacrylamide-based hydrogel lubricating coatings formed on the surfaces of different substrates in Example 3 were systematically evaluated using a friction tester (CSM, Switzerland), and compared with an uncoated blank substrate; the test was conducted with a lubricant of water, a normal phase loading of 50 mN, and a friction test antithesis of a glass ball (with a diameter of 5 mm), by a reciprocating mode (with a sliding distance of 2 mm) at a sliding frequency of 1 Hz and a test cycle of 60 times, and the results were shown in FIG. 3; as shown in FIG. 3, compared with the blank substrate, after the hydrogel lubricating coating was modified on the surfaces of different substrates by the method of the present disclosure, the friction coefficients of the surfaces were significantly reduced, indicating that the polyacrylamide-based hydrogel lubricating coating could be controllably grown on the surface of various materials by the method of the present disclosure.

FIG. 4A-D showed actual photos of a latex catheter (FIG. 4A) and its inner surface (FIG. 4B), and an optical microscope photo (FIG. 4C) and a scanning electron microscopy (SEM) image (FIG. 4D) of the polyacrylamide-based hydrogel coating on the inner surface of the latex catheter; it was seen from FIG. 4A-D that the polyacrylamide-based hydrogel lubricating coating modified on the inner surface of the latex catheter was relatively uniformly distributed, with a thickness of about 140 μm; meanwhile, an interface between the coating and the latex catheter substrate was clear, seamless and tightly combined.

The above descriptions are merely preferred implementations of the present disclosure. It should be noted that a person of ordinary skill in the art may further make several improvements and modifications without departing from the principle of the present disclosure, but such improvements and modifications should be deemed as falling within the protection scope of the present disclosure.

What is claimed is:

1. A method for modifying a hydrogel lubricating coating on a surface of general equipment, comprising the following steps:

depositing an adhesive solution of a catechol group-containing polymer on a surface of a substrate, to obtain a polyphenol coating-deposited substrate; wherein the substrate is general equipment; and compounding the polyphenol coating-deposited substrate with a hydrogel monomer solution, and conducting in-situ polymerization to obtain a hydrogel lubricating coating-modified substrate; wherein the hydrogel monomer solution comprises persulfates and transition metal ions.

2. The method according to claim 1, wherein a material of the general equipment comprises a natural material and an artificial material; and the artificial material is selected from the group consisting of an inorganic metal material, an inorganic non-metallic material, and an organic polymer.

3. The method according to claim 1, wherein in the adhesive solution, the catechol group-containing polymer is a poly(dopamine methacrylamide-methoxyethyl acrylate) copolymer; and a preparation method of the poly(dopamine methacrylamide-methoxyethyl acrylate) copolymer comprises the following steps:

mixing dopamine methacrylamide, methoxyethyl acrylate, and azobisisobutyronitrile with an organic solvent, and conducting free radical polymerization to obtain the poly(dopamine methacrylamide-methoxyethyl acrylate) copolymer; wherein the dopamine methacrylamide and the methoxyethyl acrylate have a mass ratio of (0.5-2.0):(1.0-15); and the free radical polymerization is conducted at 50° C. to 80° C. for 6 h to 18 h.

4. The method according to claim 1, wherein the adhesive solution of the catechol group-containing polymer has a solvent being one or more selected from the group consisting of methanol, ethanol, isopropanol, dichloromethane, dichloroethane, trichloroethane, N,N-dimethylformamide, dimethyl sulfoxide, N-methylpyrrolidone, tetrahydrofuran, ethyl acetate, and butyl acetate, and has a mass concentration of 1% to 50%.

5. The method according to claim 3, wherein the adhesive solution of the catechol group-containing polymer has a solvent being one or more selected from the group consisting of methanol, ethanol, isopropanol, dichloromethane, dichloroethane, trichloroethane, N,N-dimethylformamide, dimethyl sulfoxide, N-methylpyrrolidone, tetrahydrofuran, ethyl acetate, and butyl acetate, and has a mass concentration of 1% to 50%.

6. The method according to claim 1, wherein the hydrogel monomer solution comprises the following components by mass percentage: 5% to 60% of a monomer, 0.01% to 5% of a transition metal ion, 0.02% to 5% of an initiator, 0.01% to 1% of a cross-linking agent, and water as a balance.

7. The method according to claim 6, wherein the monomer is one or more selected from the group consisting of acrylic acid, methacrylic acid, acrylamide, hydroxyethyl acrylate, hydroxyethyl methacrylate, polyoxyethylene methacrylate, N-isopropylacrylamide, 2-acrylamido-2-methylpropanesulfonic acid, 2-acrylamido-2-methylpropanesulfonate, methacrylate sulfonate, chitosan acrylate, chitosan methacrylate, dimethylaminoethyl methacrylate, sodium methacrylate alginate, methacryloylethyl carboxybetaine, and methacryloylethyl sulfobetaine.

8. The method according to claim 6, wherein the initiator is potassium persulfate and/or ammonium persulfate; and the cross-linking agent is N,N'-methylenebisacrylamide and/or polyethylene glycol dimethacrylate.

9. The method according to claim 1, wherein the transition metal ion is one or more selected from the group consisting of $Fe^{3+}$, $Ag^+$, $Cu^{2+}$, $Cu^+$, $Ru^{3+}$, $Mn^{2+}$, $Co^{2+}$, and $Ni^{2+}$.

10. The method according to claim 6, wherein the transition metal ion is one or more selected from the group consisting of $Fe^{3+}$, $Ag^+$, $Cu^{2+}$, $Cu^+$, $Ru^{3+}$, $Mn^{2+}$, $Co^{2+}$, and $Ni^{2+}$.

11. The method according to claim 1, wherein the in-situ polymerization is conducted at −10° C. to 40° C. for 0.5 min to 30 min.

12. Hydrogel lubricating coating-modified general equipment prepared by the method according to claim 1, comprising general equipment and a hydrogel lubricating coating modified on a surface of the general equipment; wherein the hydrogel lubricating coating comprises a polymeric micelle-based polyphenol coating and a hydrogel coating that are sequentially laminated on the surface of the general equipment.

13. The hydrogel lubricating coating-modified general equipment according to claim 12, wherein a material of the general equipment comprises a natural material and an artificial material; and the artificial material is selected from the group consisting of an inorganic metal material, an inorganic non-metallic material, and an organic polymer.

14. The hydrogel lubricating coating-modified general equipment according to claim 12, wherein in the adhesive solution, the catechol group-containing polymer is a poly(dopamine methacrylamide-methoxyethyl acrylate) copolymer; and a preparation method of the poly(dopamine methacrylamide-methoxyethyl acrylate) copolymer comprises the following steps:
mixing dopamine methacrylamide, methoxyethyl acrylate, and azobisisobutyronitrile with an organic solvent, and conducting free radical polymerization to obtain the poly(dopamine methacrylamide-methoxyethyl acrylate) copolymer; wherein the dopamine methacrylamide and the methoxyethyl acrylate have a mass ratio of (0.5-2.0):(1.0-15); and the free radical polymerization is conducted at 50° C. to 80° C. for 6 h to 18 h.

15. The hydrogel lubricating coating-modified general equipment according to claim 12, wherein the adhesive solution of the catechol group-containing polymer has a solvent being one or more selected from the group consisting of methanol, ethanol, isopropanol, dichloromethane, dichloroethane, trichloroethane, N,N-dimethylformamide, dimethyl sulfoxide, N-methylpyrrolidone, tetrahydrofuran, ethyl acetate, and butyl acetate, and has a mass concentration of 1% to 50%.

16. The hydrogel lubricating coating-modified general equipment according to claim 12, wherein the hydrogel monomer solution comprises the following components by mass percentage: 5% to 60% of a monomer, 0.01% to 5% of a transition metal ion, 0.02% to 5% of an initiator, 0.01% to 1% of a cross-linking agent, and water as a balance.

17. The hydrogel lubricating coating-modified general equipment according to claim 16, wherein the monomer is one or more selected from the group consisting of acrylic acid, methacrylic acid, acrylamide, hydroxyethyl acrylate, hydroxyethyl methacrylate, polyoxyethylene methacrylate, N-isopropylacrylamide, 2-acrylamido-2-methylpropanesulfonic acid, 2-acrylamido-2-methylpropanesulfonate, methacrylate sulfonate, chitosan acrylate, chitosan methacrylate, dimethylaminoethyl methacrylate, sodium methacrylate alginate, methacryloylethyl carboxybetaine, and methacryloylethyl sulfobetaine.

18. The hydrogel lubricating coating-modified general equipment according to claim 16, wherein the initiator is potassium persulfate and/or ammonium persulfate; and the cross-linking agent is N,N'-methylenebisacrylamide and/or polyethylene glycol dimethacrylate.

19. The hydrogel lubricating coating-modified general equipment according to claim 12, wherein the transition metal ion is one or more selected from the group consisting of $Fe^{3+}$, $Ag^+$, $Cu^{2+}$, $Cu^+$, $Ru^{3+}$, $Mn^{2+}$, $Co^{2+}$, and $Ni^{2+}$.

20. The hydrogel lubricating coating-modified general equipment according to claim 12, wherein the in-situ polymerization is conducted at −10° C. to 40° C. for 0.5 min to 30 min.

\* \* \* \* \*